(12) United States Patent
Crane et al.

(10) Patent No.: US 8,649,848 B2
(45) Date of Patent: Feb. 11, 2014

(54) SYNCHRONIZATION OF ILLUMINATION SOURCE AND SENSOR FOR IMPROVED VISUALIZATION OF SUBCUTANEOUS STRUCTURES

(75) Inventors: Robert L. Crane, Kettering, OH (US); Michael P. Buchin, Palo Alto, CA (US)

(73) Assignee: The United States of America, as represented by the Secretary of the Air Force, Washington, DC (US)

( * ) Notice: Subject to any disclaimer, the term of this patent is extended or adjusted under 35 U.S.C. 154(b) by 1343 days.

(21) Appl. No.: 11/548,313

(22) Filed: Oct. 11, 2006

(65) Prior Publication Data

US 2007/0276258 A1  Nov. 29, 2007

Related U.S. Application Data

(60) Provisional application No. 60/786,880, filed on Mar. 28, 2006.

(51) Int. Cl.
*A61B 6/00* (2006.01)
*G02F 1/01* (2006.01)

(52) U.S. Cl.
USPC ............................. 600/476; 600/473; 250/330

(58) Field of Classification Search
None
See application file for complete search history.

(56) References Cited

U.S. PATENT DOCUMENTS

| | | | |
|---|---|---|---|
| 3,962,600 A | 6/1976 | Pittman | |
| 4,817,622 A | 4/1989 | Pennypacker et al. | |
| 4,953,539 A | 9/1990 | Nakamura et al. | |
| 5,241,170 A | 8/1993 | Field, Jr. et al. | |
| 5,417,688 A | 5/1995 | Elstrom et al. | |
| 5,519,208 A | 5/1996 | Esparza et al. | |
| 5,954,644 A | 9/1999 | Dettling et al. | |
| 6,032,070 A | 2/2000 | Flock et al. | |
| 6,230,046 B1 * | 5/2001 | Crane et al. | 600/476 |
| 6,272,374 B1 | 8/2001 | Flock et al. | |
| 6,556,858 B1 | 4/2003 | Zeman | |
| 6,597,941 B2 | 7/2003 | Fontenot et al. | |
| 6,748,259 B1 | 6/2004 | Benaron et al. | |
| 2004/0215081 A1 | 10/2004 | Crane et al. | |
| 2005/0157203 A1 * | 7/2005 | Nakakuki et al. | 348/362 |
| 2006/0173351 A1 * | 8/2006 | Marcotte et al. | 600/473 |
| 2006/0291049 A1 * | 12/2006 | Juenger et al. | 359/443 |
| 2007/0073160 A1 * | 3/2007 | Imam | 600/476 |

* cited by examiner

*Primary Examiner* — Long V. Le
*Assistant Examiner* — Angela M Hoffa
(74) *Attorney, Agent, or Firm* — Hasse & Nesbitt LLC; Daniel F. Nesbitt

(57) ABSTRACT

System and method are described for synchronizing a pulsed source of the near infrared illumination used in visualizing subcutaneous structures with the background illumination normally extant in medical treatment settings that allow both enhanced image acquisition and use of higher power pulsed infrared illumination sources.

25 Claims, 4 Drawing Sheets

SYNCHRONIZATION OF ILLUMINATION SOURCE AND SENSOR FOR IMPROVED VISUALIZATION OF SUBCUTANEOUS STRUCTURES

CROSS REFERENCE TO RELATED APPLICATION

This application claims priority of the filing date of Provisional Application Ser. No. 60/786,880 filed Mar. 28, 2006.

STATEMENT OF GOVERNMENT INTEREST

The invention described herein was made under a Cooperative Research and Development Agreement number 02-161-ML-01 with the Department of The Air Force. The Government of the United States has certain rights in the invention.

FIELD OF THE INVENTION

The invention described herein relates generally to medical devices and procedures for access to human or animal vasculature, and more particularly to system and method for enhanced visualization of subcutaneous structures under ambient lighting from fluorescent, incandescent, light emitting diode (LED) or other illumination source.

BACKGROUND OF THE INVENTION

The use of near infrared (NIR) radiation for diagnostic procedures in the human body has traditionally been limited by the inability to transmit NIR radiation into and through the body and extremities (see, for example, *Handbook of Optical Biomedical Diagnostics*, V Tuchin, Ed, SPIE Press, Bellingham Wash. (2002)). U.S. Pat. No. 6,230,046 to Crane et al showed that with sufficient amplification, transmitted NIR illumination may be used for both diagnostic and medical procedures involving vascular imaging. However, with this amplification, the imaging system must use a darkened environment and bandpass filters to limit interference from background light typically extant in medical settings.

The use of an NIR sensor and reflected or transilluminated NIR light to view both dermal and subdermal structures in the body is limited by the amount of light that is interacted with the body and is available for imaging on a detector, such as those commonly used in the art including charged coupled device (CCD) arrays, metal on silicon (MOS) arrays or image intensifier tubes (IIT) or combination of these. Image quality or resolution is directly related to the amount of light with image information that reaches the detector after interaction with the body minus the light that is captured that does not interact with the body. Light that does not contain image information is considered noise and degrades the image. For example, sunlight that is reflected from the surface of skin and entering the detector optics degrades the image in direct relationship to the amount of light intercepted by the detector.

Optical filtering to restrict the pass band of the detector to the light emitted by the illumination source according to Crane et al showed that NIR sensitive detectors could be used to image both dermal and subdermal structures such as veins and arteries. This works well for many illumination sources of visible lighting, but has limited applicability for sources that emit light in that portion of the NIR spectrum near or within the band used for image formation. Typical visible illumination sources such as fluorescent light bulbs have strong emission lines at wavelengths between 800 and 900 nm that represent noise in an NIR subdermal imaging system.

SUMMARY OF THE INVENTION

The invention described herein solves or substantially reduces in critical importance problems in the prior art by providing system and method for NIR imaging of subcutaneous structures under full fluorescent lighting including use of higher power illumination sources to transilluminate thicker human tissue. System and method are described for synchronizing a pulsed source of the NIR light used in visualizing subcutaneous structures with the background lighting normally extant in medical treatment settings that allow both enhanced image acquisition and use of higher power pulsed infrared illumination sources. The background lighting may also have as its source fluorescent light or white light LEDs used to illuminate the medical treatment procedure.

In accordance with an aspect of the invention it was recognized that fluorescent light is emitted from a source in a full wave rectified sine wave series of peaks at a frequency of 120 Hz. The detector is time gated to eliminate extraneous light, and NIR imaging is accomplished while the fluorescent lighting is extinguished at 120 Hz. When the image illumination is captured during these small windows of darkness and near darkness, image quality is enhanced to nearly that obtained under substantially complete darkness.

Pulsing the illumination source (light emitting diodes (LED), etc) and the detector in synchronization with the background illumination (for example, fluorescent) according to the invention allows an increase in electrical power that can be applied to the LED illumination source (with corresponding brighter light output) and optimizes the imaging data during the time that the background illumination is diminished or extinguished. This offers a benefit of significantly enhanced user facility in that the imaging system can be used in a fully fluorescent room light illumination. Standard fluorescent bulbs were used as background lighting in demonstration of the invention, but other pulsed sources such as visible LEDs may be used within the scope of the invention and the appended claims.

The pulsed aspect of the invention additionally provides significantly enhanced power levels that can be applied to the illuminating source while keeping its temperature within appropriate bounds for efficient power conversion, e.g. in light emitting diodes. Further, this technique significantly reduces the temperature of the lighting package when it is a necessary or optimal part of an illumination source that must be in contact with patients.

The invention finds use in medical procedures that require access to or imaging of subdermal structures for various medical procedures, such as, but not limited to, venous and arterial access, including access under hazardous or dimly lit conditions, detection of subcutaneous foreign structures, placement of medical devices for injection or removal of fluids or other procedures as would occur to the skilled artisan practicing the invention, including blood sampling or administration of therapeutic agents, the placement of a hypodermic needle for taking a fluid sample from a suspected tumor or growth in the human female breast, which is not usually aided by real time imaging, or placement of other surgical instruments, such as catheters, prostheses, small endoscopic instruments and others. The invention permits continual imaging during this procedure so that placement of the medical device is maintained within the area of interest, which is not practical with conventional x-ray imaging due to the exposure of the patient and clinicians to excessive ionizing radiation.

The invention can also be used in association with controlled pulsed visible environmental lighting, such as pulsed white light LED lighting, wherein the pulse length and period of lighting mode is controlled Wavelength selection can be made for visualization of selected subcutaneous structures, such as visualizing veins from arteries, and applied for reflection, transillumination or backscatter modes.

The invention therefore relates to an improved medical procedure for enhancing the visualization of veins, arteries and other subcutaneous natural or foreign structures in the body, under conditions of artificial lighting, comprising the steps of:
  providing a light source for illuminating a portion of the body in at least one of a reflection mode and a transillumination mode, and illuminating the portion of the body with said light source;
  detecting the pulsed output of the artificial lighting, whether environmental or artificially applied in conjunction with the practice of the method, and under which the method is performed, and defining the maxima and minima of the output of the artificial lighting;
  pulsing said light source in synchronization with the minima of the output from the artificial lighting; and
  detecting the light from said light source reflected from or transilluminated through the body portion.

The invention also relates to a system for enhancing the visualization of veins, arteries and other subcutaneous natural or foreign structures in the body, under conditions of artificial lighting, comprising:
  a light source for illuminating a portion of the body in at least one of a reflection mode and a transillumination mode;
  first light detection means for detecting the pulsed output of the artificial lighting, and defining the maxima and minima of the output of the artificial lighting;
  means for pulsing said light source and means for synchronizing the pulsing of said light source with the minima of the output of the artificial lighting; and
  second light detection means for detecting the light from said light source reflected from or transilluminated through the body portion.

The invention further relates to a system for visualizing a structure inside a body portion, the system comprising:
  an illumination source for illuminating a body portion, which may be in the range of about 400 to 1400 nm, and which may be pulsed in a frequency range of abut 10 Hz to 10 kHz;
  a receiver for receiving light from the body portion during at least two discrete temporal intervals, and a light intensifier coupled to the receiver; and
  a display that displays an image including information about the structure, and, alternatively a detector for detecting background illumination, and a source controller in communication with the detector for selectively synchronizing the source illumination with a temporal feature of the background illumination, and/or a receiver controller in communication with the detector for selectively synchronizing the source illumination with a temporal feature of the background illumination.

These and other aspects, objects, and advantages of the invention will become apparent from the following detailed description of representative embodiments thereof

DESCRIPTION OF THE DRAWINGS

The invention will be more clearly understood from the following description of representative embodiments thereof read in conjunction with the accompanying drawings.

DETAILED DESCRIPTION OF THE INVENTION

Figure 1:
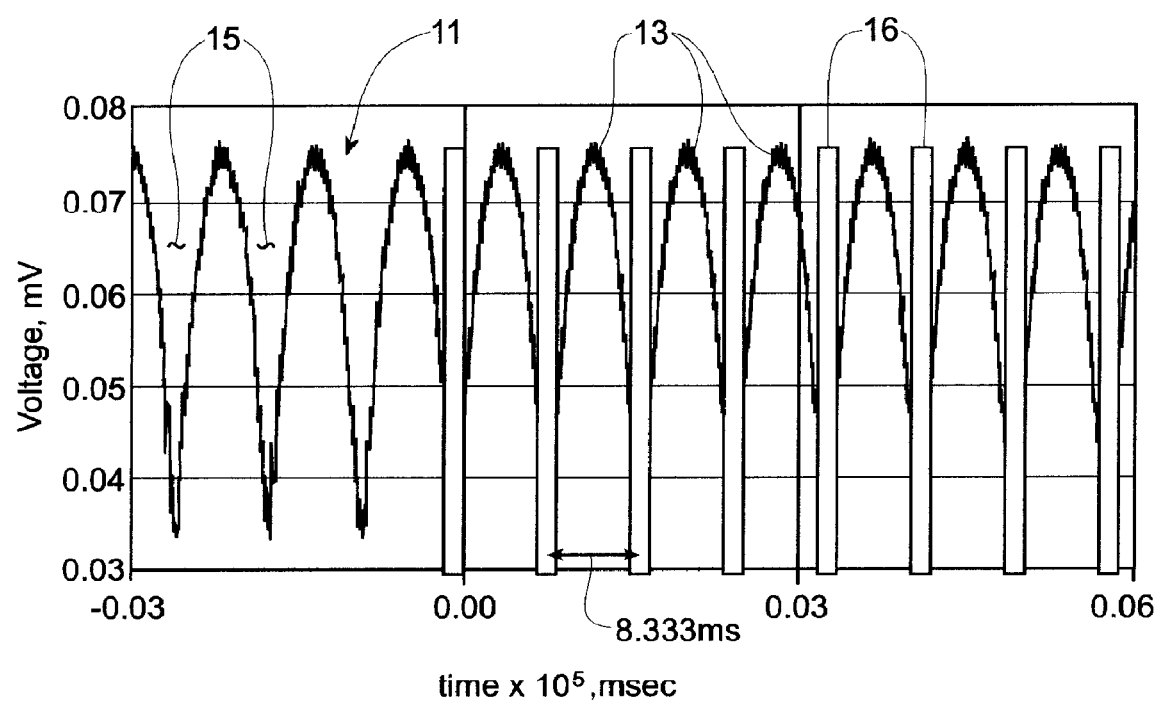
FIG. 1 shows the optical power output from a typical fluorescent light bulb with a superimposed pulse train representing the output of an LED light source and data acquisition times for an image acquisition system for NIR imaging of subdermal structures according to the invention.

Referring now to the drawings, FIG. 1 shows a plot 11 of voltage versus time defining the optical power output from a typical commercially available fluorescent light bulb. Background lighting in a medical treatment environment may have as its source incandescent, LED, or other pulsed illumination, as well as fluorescent illumination. The invention is, however, described herein in consideration of fluorescent background lighting as representative of the lighting under which the invention may be operative, with the understanding that the invention can be practiced, within the scope of these teachings and the appended claims, under conditions of other pulsed lighting.

In accordance with a feature of the invention, and considering fluorescent background lighting as an example, it is recognized that fluorescent illumination is produced as a full wave rectified sine wave with a frequency of 120 Hz. If the artificial lighting is applied in conjunction with the practice of the invention, the lighting need not be a sine wave or rectified wave. The illumination is produced in pulses 13 between which are defined intervals 15 during which the illumination is off or substantially diminished in intensity. In accordance then with a governing principle of the invention, NIR illumination of subcutaneous structures, as from an LED source, is accomplished in pulses 16 applied during intervals 15. Pulsing of the NIR source is synchronized to provide maximum NIR output when ambient (fluorescent) illumination is minimum or extinguished. The synchronization pulse also gates the NIR imaging detector so that image data is acquired only during intervals 15 when ambient (room) lighting is at a minimum. A synchronization frequency of 120 Hz is well above the human flicker fusion frequency of 30 Hz so that the images appear continuous. Optimum pulse timing and duration can be easily ascertained by one skilled in the art practicing the invention. Depending on the type of background illumination, pulse timing may be selected corresponding to the frequency of the background that may be in the range of from about 10 Hz to about 10 kHz. Pulse duration may be of the order of the intervals 15. In the example represented in FIG. 1, the fluorescence has a cycle of about 833 msec, and permits about 211 msec (about 25%) for a duty cycle for NIR pulses 16. Shorter duty cycles for NIR pulsing may be associated with larger currents applied to the NIR source. The timing or gate width of the NIR detector, represented by the width of pulses 16, can be varied to present to the observer both a surface image using visible light and a subsurface image either separately or simultaneously.

Figure 2:
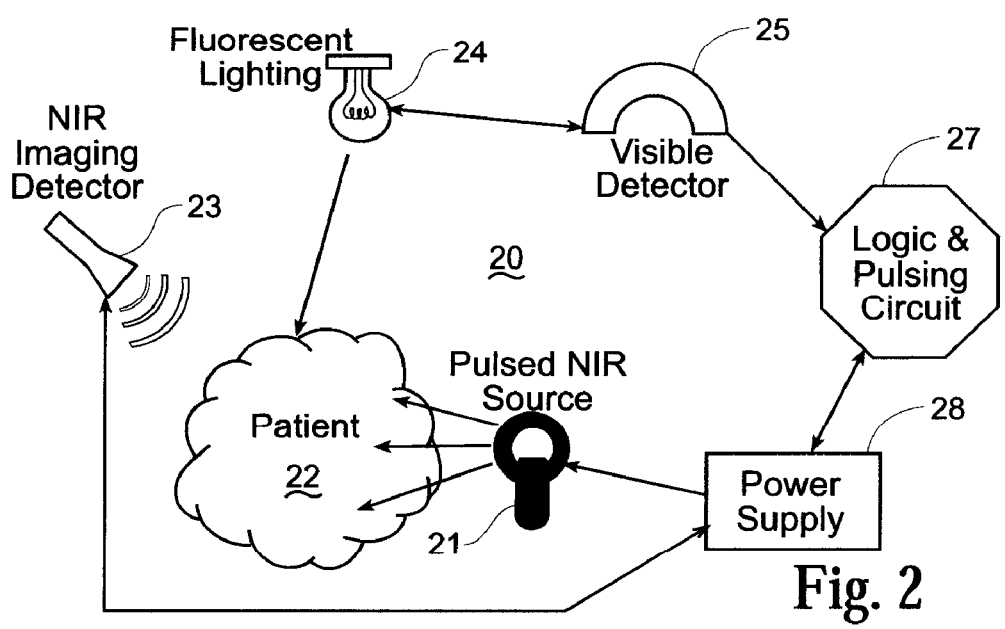
FIG. 2 is a schematic of the key elements of a pulsed NIR imaging system useful in the practice of the invention.

Referring now to FIG. 2, shown therein is a schematic of the essential elements of a pulsed NIR imaging system 20 for practicing the method of the invention as just described. In system 20, NIR source 21 is used to illuminate or transilluminate a body portion of patient 22 with images thereof received by NIR imaging detector 23 similarly to the method described by Crane et al. Source 21 may most usefully have wavelength in the range of about 400 nm to abut 1400 nm, selected as would occur to the skilled artisan practicing the invention. In accordance with the present invention, however, and distinct from the Crane et al method, source 21 is pulsed in order to provide images synchronized with the minima of the output from the ambient room (e.g., fluorescent, visible LEDs) light source 24. To accomplish this, a visible detector 25 is provided to detect the output of light source 24 and a logic and pulsing circuit 27 interconnects detector 25 and power supply 28 to provide the synchronized pulsing to NIR source 21.

Figure 3:
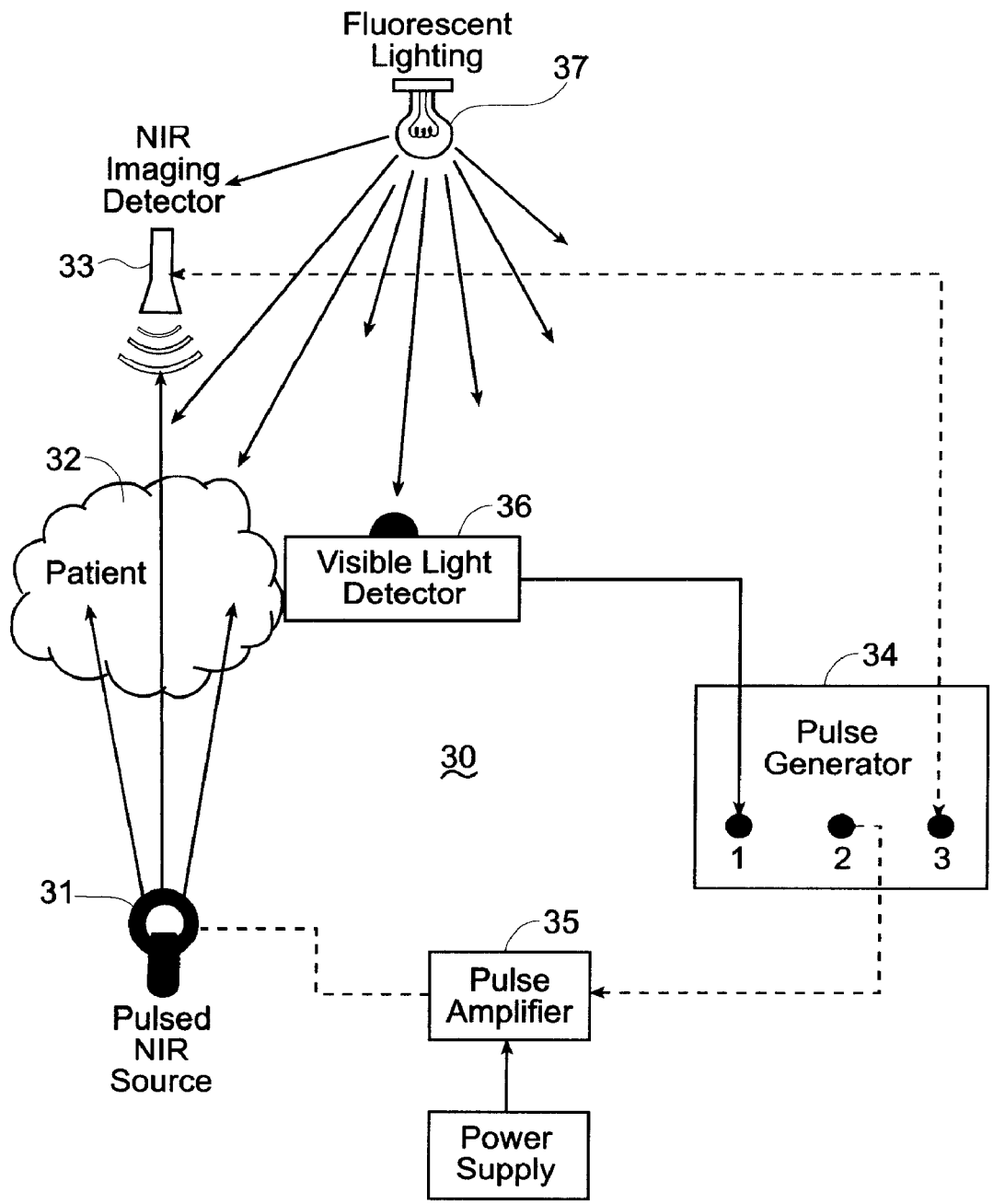
FIG. 3 is a detailed schematic of the system components useful in pulsed NIR imaging according to the invention.

Referring now to FIG. 3, shown therein is a more detailed schematic of the essential components of a pulsed NIR imaging system according to the invention. In FIG. 3, system 30 includes an source 31 used to illuminate or transilluminate a body portion of patient 32 with images thereof received by NIR imaging detector 33. Source 31 is pulsed by pulse generator 34 through pulse amplifier 35. Visible light detector 36 is operatively connected with pulse generator 34 and detects the light from the ambient visible room light source 37 in order to synchronize the pulses of NIR source 31 with the minima of the output from room light source 37. In a system built and operated in demonstration of the invention, NIR source 31 was a specially built NIR light emitting diode array manufactured by Opto Technology, Inc., pulse generator 34 was a Model 9514 manufactured by Quantum Corporation, pulse amplifier 35 was a model PP600 manufactured by Gardasoft Vision, light detector 36 was an intensified CCD based camera manufactured by Stanford Photonics, Inc., these items being commercially available, not considered limiting of the invention as being selectable by the skilled artisan guided by these teachings. Other NIR sources may be used in the practice of the invention, including LEDs, xenon light source with a narrow band of light transmitted to the point of interest via a light pipe or fiber optic cable, a suitable narrow band light source or filtered, chemical based light source such as chemical or chemiluminescent sources or otherwise spectrally limited light broad band illumination source, the same not considered limiting of the invention. In the demonstration system, the entire electronic elements of the light detection and pulse generating and timing circuitry can be reduced to a single circuit board that can be housed in a compact housing for convenience of the clinical operator. A few controls that permit determination of optimum light levels and timing of the NIR light pulses and imaging detector would result in optimum images with a minimum of interaction with the imaging system. Power to the NIR light source may have a significantly different phase (as much as 60°) than that to the ambient (fluorescent) lighting because the two power sources may be derived from different legs of a three-phase commercial power source. The invention provides for such a phase difference by synchronizing the pulsing of the NIR illumination source and detector with the visible light minima using a local photo detector and pulsing circuitry as suggested in FIGS. 2 and 3.

Figure 4:
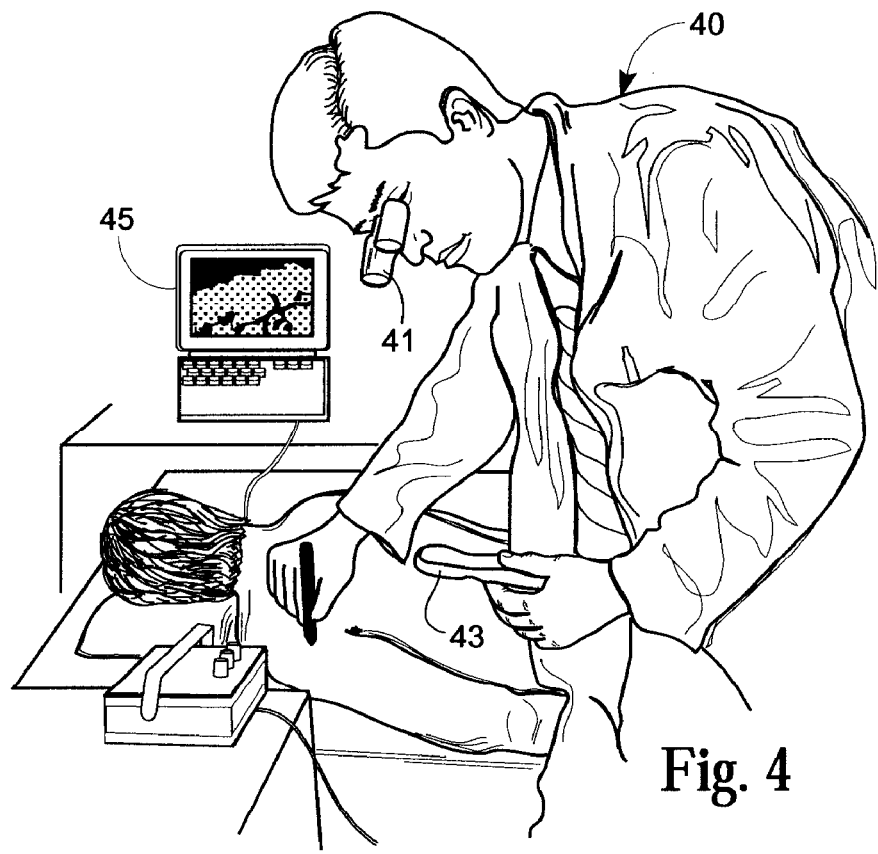
FIG. 4 is a pictorial representation of the NIR imaging method of the invention.

FIG. 4 shows a pictorial representation of a clinical use of NIR imaging method according to the invention. In FIG. 4, a medical professional 40 demonstrates the use of three different modes of visualization, namely, direct observation with image intensifier based night vision goggles (NVG) 41, an image projected on a hand held screen, such as LCD display 43, or an image displayed on a computer screen 45 remote from the patient.

State of the art NVGs have pulse regulated power supplies that accommodate a wide range of scene illuminations, including day time light levels. The pulsing and gating technique suggested by the invention may also be adapted to control the response of a solid state focal plane array, such as a charge coupled device (CCD), of many commercial and consumer grade video recorders for use over a wide range of lighting conditions. Varying pulse width allows control of both brightness of the image with a consumer grade camcorder and the image produced by the NIR system described herein. Varying the width of the imaging pulse sync signal and/or phase relationship between the pulse train and the fluorescent lighting allows control of the NIR image brightness compared to the brightness of the visible light image of the skin surface of the patient.

Figure 5:
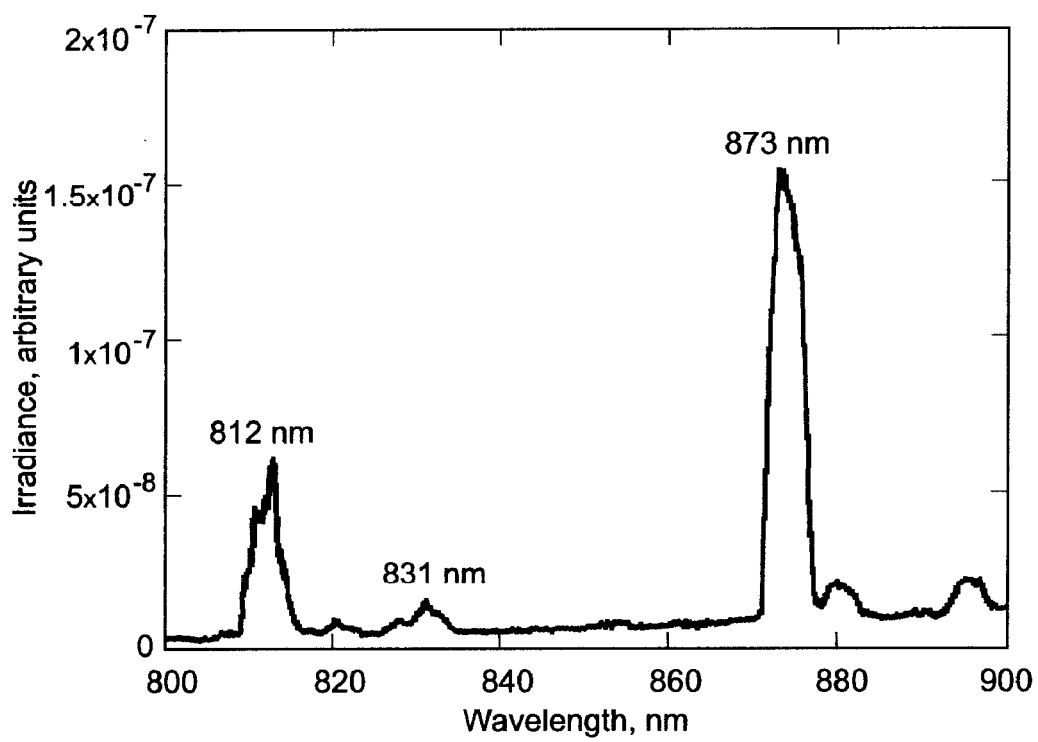
FIG. 5 is a partial irradiance spectrum from fluorescent lights typically used in an industrial environment.

FIG. 5 is a representative spectrum of a commercially available industrial fluorescent light source typical of that used in most industrial and hospital settings. Strong peaks in the spectrum at 812, 831 and 873 nm are evident. In the practice of the invention described herein it is therefore highly desirable, but not necessary, to avoid NIR illumination at these peaks, which is easily accomplished with optical filters and absorbing elements added to the NIR optical system, as would occur to the skilled artisan practicing the invention and guided by these teachings.

Figure 6:
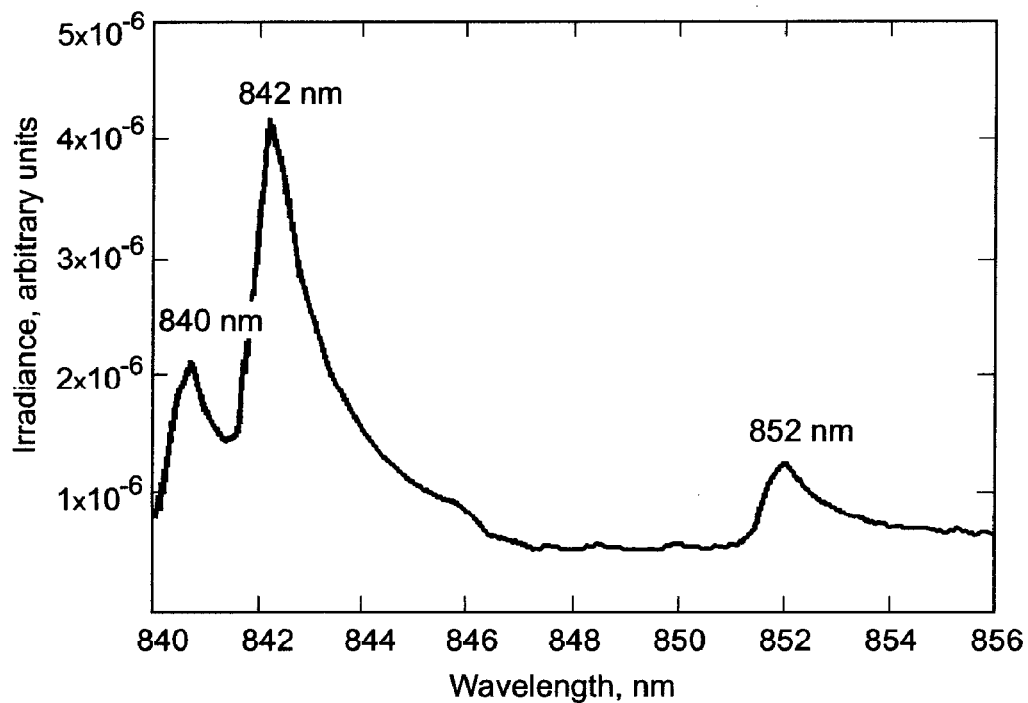
FIG. 6 is a partial irradiance spectrum from fluorescent lights typically used in a home environment.

FIG. 6 is a portion of a representative spectrum of fluorescent lights typically used in a home environment showing characteristic spectral content near 850 nm in the NIR region. In the NIR imaging, the peaks at 840, 842 and 852 nm should be avoided, such as by using optical filters and absorbing elements added to the NIR optical system.

Tests in demonstration of the invention has shown operability over a very broad range of optical powers or current and or voltage delivered to the light generating device (LED, laser diode, or other suitable light emitting device), and of duty cycles and phase relationships between the detector and pulsed light source and room illumination. NIR illumination levels sufficient for transillumination of the forearm of an adult male can be achieved with a duty cycle of as little as 0.70%. Subsurface images may be produced with a duty cycle in the range from 0.01% up to 30% depending upon the power levels delivered to the NIR light source and the levels of visible room illumination. The pulse frequency may be varied between 15 and 120 Hz and yield sufficiently continuous images for detection of both surface and subsurface anatomical features and foreign materials, diagnostic procedures, and various medical interventions (venous and arterial access, catherizations, probing for shrapnel or other foreign objects, or for non-native tissue such as tumors, etc). Additional image processing techniques, such as digital imaging processing, edge detection algorithms, could be applied to these systems to further enhance the image for analysis or diagnostic applications.

The invention therefore allows NIR imaging of subcutaneous structures under standard ambient lighting conditions, and permits use of a high light output NIR source in contact with the skin of a patient without unacceptable heating. With the higher power illumination sources, deeply buried structures may be imaged for pathological conditions such as deep veins for thromboses, and optical absorption by intervening tissue is substantially obviated.

The invention therefore provides novel system and method for enhanced visualization of subcutaneous structures under normal ambient lighting conditions from fluorescent, incandescent, light emitting diode or other illumination sources. It is understood that modifications to the invention may be made as might occur to one with skill in the field of the invention within the scope of the appended claims. All embodiments contemplated hereunder that achieve the objects of the invention have therefore not been shown in complete detail. Other embodiments may be developed without departing from the spirit of the invention or from the scope of the appended claims.

What is claimed is:

1. A method for imaging of subcutaneous natural structures including veins or arteries or subcutaneous foreign structures in a human or animal body under ambient artificial lighting that produces a pulsed visible light output having light intensity maxima and minima in the output, the method comprising the steps of:
   (a) providing an illumination source configured to illuminate a human or animal body portion containing subcutaneous natural structures including veins or arteries or subcutaneous foreign structures;
   (b) illuminating said body portion with illumination from said illumination source from outside the body;
   (c) detecting the pulsed visible light output of the ambient artificial lighting, and defining the maxima and minima of said pulsed visible light output of said ambient artificial lighting;
   (d) pulsing said illumination source in synchronization with the minima of said pulsed visible light output from said ambient artificial lighting;
   (e) detecting the illumination received from said pulsed illumination source that is reflected from, backscattered from or transilluminated through said body portion at the minima of said pulsed visible light output of said ambient artificial light ; and
   (f) producing an image from the detected illumination.

2. The method of claim 1 wherein illumination from said illumination source is in the wavelength range of about 400 to 1400 nm.

3. The method of claim 2 wherein said illumination source is selected from the group consisting of a light emitting diode, a laser diode, and a xenon source.

4. The method of claim 1 wherein the step of detecting is gated in synchronization with the pulsing of said illumination source.

5. The method of claim 4 wherein illumination from said illumination source is near infrared (nIR) illumination.

6. The method of claim 5 wherein the step of detecting consists of generating an nIR-illuminated image of the body portion that visualizes the subcutaneous natural structures including veins or arteries or subcutaneous foreign structures in the human or animal body portion that is transilluminated with the nIR illumination.

7. The method of claim 4 wherein the step of gating includes a gate width of detection of the image detector, wherein the gate width is sufficient to also detect a surface image of the human or animal body using the pulsed visible light output of the ambient artificial lighting.

8. The method of claim 1 wherein said illumination source is pulsed in the range of about 10 Hz to 10 kHz.

9. The method of claim 1 further comprising the step of displaying the image of the detected illumination.

10. The method of claim 1 wherein the step of detecting is gated in synchronization with the minima of the pulsed visible light output from the ambient artificial lighting.

11. The method of claim 1 wherein the step of detecting uses an image detector selected from the group consisting of a charged coupled device array, a metal on silicon array, and an image intensifier tube.

12. A system for enhancing the visualization of subcutaneous natural structures including veins or arteries or subcutaneous foreign structures in a human or animal body under ambient artificial lighting that produces a pulsed visible light output having light intensity maxima and minima in the output, comprising:
   (a) an illumination source configured to illuminate a human or animal body portion containing subcutaneous natural structures including veins or arteries or subcutaneous foreign structures with illumination from outside the body;
   (b) a visible light detector configured to detect the pulsed visible light output of the ambient artificial lighting, and to define the maxima and minima of said pulsed visible light output of said ambient artificial lighting;
   (c) a logic and pulsing circuit configured to pulse the illumination of said illumination source and to synchronize the pulsing of the illumination of said illumination source with the minima of said pulsed visible light output of said ambient artificial lighting; and
   (d) an imaging detector configured to detect the illumination received from said illumination source that is reflected from, backscattered from or transilluminated through the said body portion.

13. The system of claim 12 wherein illumination from said illumination source is in the wavelength range of about 400 to 1400 nm.

14. The system of claim 13 wherein said illumination source is selected from the group consisting of a light emitting diode, a laser diode, and a xenon source.

15. The system of claim 12 wherein said imaging detector is selected from the group consisting of a charged coupled device array, a metal on silicon array, and an image intensifier tube.

16. The system of claim 12 wherein the logic and pulsing circuit is further configured to gate said imaging detector in synchronization with said pulsing of the illumination of said illumination source.

17. The system of claim 12 wherein the logic and pulsing circuit pulses said illumination source in the range of about 10 Hz to 10 kHz.

18. The system of claim 12 further comprising a display operatively connected to said imaging detector for displaying an image of the received illumination.

19. The method of claim 12 wherein illumination from said illumination source is near infrared (nIR) illumination.

20. The system of claim 12 wherein the logic and pulsing circuit is further configured to gate said imaging detector in synchronization with the minima of the pulsed visible light output from the ambient artificial lighting.

21. A system for visualizing a subcutaneous structure inside a human or animal body portion, the system comprising:
   (a) an illumination source configured to illuminate a human or animal body portion with illumination from outside the body;
   (b) a receiver configured to receive light from the illumination source that is reflected from, backscattered from or transilluminated through the body portion during at least two discrete temporal intervals;
   (c) a first light detector coupled to the receiver;
   (d) a second light detector configured to detect a pulsed visible light output of light from an ambient artificial lighting having an intensity maxima and minima in the output,
   (e) a controller selected from a source controller and a receiver controller, in communication with said second light detector and configured to selectively synchronize the illumination of the illumination source received during the at least two discrete temporal intervals with a temporal interval during the intensity minima of the detected pulsed visible light output from the ambient artificial lighting; and (f) a display operatively connected to said first light detector, configured to display an image comprising the light reflected from, backscattered from or transilluminated through the body portion including information about subcutaneous structures inside the body portion.

22. The system of claim 21 wherein the illumination from said illumination source is in a wavelength range of from about 400 nm to about 1400 nm.

23. The system of claim 22 wherein the controller pulses said illumination source at a frequency in the range of from about 10 Hz to 10 kHz.

24. The system of claim 22 wherein the controller pulses the illumination of the illumination source with a pulse time duration of substantially the length of the temporal interval of the intensity minima of the detected pulsed visible light output from the ambient artificial lighting.

25. The method of claim 21 wherein illumination from said illumination source is near infrared (nIR) illumination.

* * * * *